(12) United States Patent
Hacker et al.

(10) Patent No.: US 6,391,631 B1
(45) Date of Patent: May 21, 2002

(54) BACTERIAL PLASMIDS

(75) Inventors: Jörg Hacker, Gerbrunn; Ulrich Sonnen-Born, Bochum; Jürgen Schulze, Bergholz-Rehbrücke; Gabrielle Blum-Oehler, Würzburg; Jürgen Malinka, Selm; Hans Proppert, Hagen, all of (DE)

(73) Assignee: Pharma-Zentral, Herdecke (DE)

( * ) Notice: Subject to any disclaimer, the term of this patent is extended or adjusted under 35 U.S.C. 154(b) by 0 days.

(21) Appl. No.: 09/676,974

(22) Filed: Oct. 2, 2000

Related U.S. Application Data (62) Division of application No. 09/402,039, filed as application No. PCT/EP98/01720 on Apr. 1, 1998.

(30) Foreign Application Priority Data

Apr. 2, 1997 (DE) .......................................... 197 13 543

(51) Int. Cl.[7] .................. C12N 15/63; C12N 15/00; C12Q 1/68; C07H 21/04; A61K 48/00
(52) U.S. Cl. .................. 435/320.1; 435/6; 435/69.1; 435/252.3; 536/23.1; 514/44
(58) Field of Search .................. 536/23.1; 514/44; 435/6, 320.1, 69.1, 252.3

(56) References Cited

PUBLICATIONS

Cannon, P. M. et al.: "Complete nucleotide sequence and gene organization of plasmid NTP16." PLASMID, vol. 27, No. 3, May 1992, pp. 220–230, XP002085747.

Stieglitz, H. et al.: "Identification of a 2–Md Plasmid from *Shigella flexneri* associated with reactive arthritis." ARTHRITIS AND RHEUMATISM, vol. 32, No. 8, Aug. 1989, pp. 937–946, XP002085748.

Stirling, C.J. et al.: "The arginine repressor is essential for plasmid–stabilizing site–specific recombination at the ColE1 cer locus." EMBO Journal, vol. 7, No. 13, 1998, pp. 4389–4395, XP002085749 & Database EMBL—EMPRO entry Pccg1, Acc. No. J01566; M33100, Feb. 15, 1992. "Plasmid ColE1, complete genome." XP002085751.

Yasueda, H. et al.: "Structural and functional organization of colE2 and ColE3 replicons" MOLECULAR AND GENERAL GENETICS, vol. 215, 1989, pp. 209–216, XP002094006.

Boyd, A.C. et al.: "Characterization of the ColE1 mobilization region and its protein products" MOLECULAR AND GENERAL GENETICS, vol. 217, 1989, pp. 488–498, XP002094007.

Blum, G. et al.: "Properties of *Escherichia coli* strains of serotype 06." INFECTION, vol. 23, No. 4, Jul. 1995, pp. 234–236, XP002085750.

*Primary Examiner*—David Guzo
*Assistant Examiner*—Gerald G. Leffers, Jr.
(74) *Attorney, Agent, or Firm*—Pillsury Winthrop LLP (57) ABSTRACT

*E. coli* plasmids pMUT 1 and pMUT 2 containing DNA sequences exhibiting significant homologies to reduplicaton starting positions of other enterobacterial plasmids are disclosed. Also disclosed are expression vectors containing plasmicis pMUT1 and pMUT 2.

6 Claims, 11 Drawing Sheets

FIG. 1(a)

```
HindIII
agcttttaga gcttggatac catgacccaa tgaagctacc tcaaaacttt gaatgatcga   60
gcggcaggct aaatgaaatc ttgagattca ttcagtctcg tcgtaatctc actattgtaa  120
aaacgaaaaa accaccctgg caggtggttt ttcgaaggtt agttaatcct ggcagattct  180
ctaaccgtgg taacagtctt gtgcgagaca tgtcaccaaa tactgtcctt tcagtgtagc  240
ctcagttagg ccgccacttc aagaactctc gttacatctc tcgcacatcc tgcttaccag  300
tggccgttgc cagtggcgtt aagtcgtgtc ttaccgggtt ggactcaaga cgatagttac  360
cggataaggc gccaggtcgg gctgaacggg gggttcgtgc acacagccca gcttggagcg  420
aacgacctac accgaacctg agatacctaa cagcgtgacg tatgagaaag cgccacgctt  480
cccgaagaga aaggcggaca ggtatccggt aagcggcagg gtcgaacagg gagagcgcac  540
gagggagctt ccagggggaa acgcctggta tctttatata gtcctgtcgg gtttcgccac  600
ctctgacttg agcgtcgatt tttgtgatgc tcgtcagggg gtcgaggcct atggaaaaag  660
cctcccgcgg agaccccttc ttctgggatc tttgtctttt gctcacatgt tctttccggt  720
tttatccccc gattctgtgg ataacgtat taccgccttt gagtgagctg acaccgctcg  780
ccgcagtcga acgaccgagc gtagcgagtg agtgagcgag gaagcggaag agagaattta  840
tgtgacattt tctccttacg ctccctctatg ccgttctgca tcctgtccgg atgcgttata  900
tcccggtaag atttccgct tcaaagcgtg tctgtatgct gttctgcgga tcttctgcga  960
gttcgtgcag tttctcacac atggcggcct gttcgtcggc attggtgcg tccagttttt 1020
cgagcagcgt caggctctga ctttttatga atcccgccat gttgagtacg gcttgctgct 1080
gcttattcat cttttcgttt tctccgttct gtctgtcatc tgcgttgtgt gattatatcg 1140
```

FIG. 1(b)

```
cgtaccactt ttcgactgtt ttgctgccgc tattctgccg cttggctttt tgacgggcat  1200
ttctgtcaga caacactgtc actgccaaaa aactgccgtg cctttgtcgg taattcgagc  1260
ttgctgacag gacaggatgt gcaattgtta taccgcgcat acatgcacgc tattacaatt  1320
gccctggtca ggctttgccc cgacacccat gtcagatacg gagccatgtt ttatgacaaa  1380
acgaagtgga agtaatacgc gcaggcgggc tatcagtcgc cctgttcgtc tgacggcaga  1440
agaagaccag gaaatcagaa aaagggctgc tgaatgcggc aagaccgttt ccggttttt   1500
tcgggcggca gctctctggta agaaagttaa ctcactgact gatgatcggg tactgaaaga  1560
agttatgaga ctggggcgt  tacagaaaaa actctttatc gacggcaagc gtgtcgggga  1620
cagggagtat gcggaggtgc tgatcgctat tacggagtat caccgtgccc tgttatccag  1680
gcttatggca gattagcttc ccggagagaa aactgtcgaa aactgacggt atgaacaccg  1740
taagctccca aagtgatcac cattcgcttt catgcatagc tatgcagcga gctgaaacga  1800
tcctgacgca tccttcctgt ttttccgggg taaaacatct cttttgcgg  tgtctcgcgt  1860
cagaatcgcg ttcagcgcgt ttcagtggtg cgtacaatta agggattatg gtaaatatat  1920
gagctatgcg ataactttaa ctgtgaagcg atgaacccat tacaggcaaa gccaattact  1980
cctgacagtg aagcaggcag aagcagggct accaagacca atgcaataag taatatatcg  2040
```

FIG. 1(c)

```
tttgctatc gtgccatccg tcgcgctcag ttccattgtg cttttttaag ctgtcgtttt 2100
tcttacgta tataccggtt ttttatggcg tggtttctta acttgttcag ctactgatgg 2160
acccatgtat ctagtagtc aactagcttt gttagatcat aaaatattgc gaccaccata 2220
tcggcgatca ctcttcgatg ttggtttctt gtccaagaga ttagctttt caagatcatt 2280
gatagctctc tgaacagtcc gtacagaaac cccatacgt atggctagac tttccattga 2340
cggatgcggc cactcttgca aactccacca gtgaacgatc aggttaagta gtgtgttaaa 2400
ggccactgaa gttagctttt tctcgttttg tataaaaaac aatacggtag gcactgctgt 2460
ccagccaaga gacaaaccgc cagctttcca tttattctta acggagtaag tcattgattt 2520
tcctaagccc caaatatatt aaagtatata ttatatgtat attcatatga ataggggtgac 2580
actggcgcca ttattgtgca accaaaaaag actactctga aaacgaggaa aagattttt 2640
cctgcctgaa ttagatacgg agttagcgat atgaaaaccg aacaacgtca tgatccttgtt 2700
aaagatattg aggtttttgg cgtatccttg tctctgttga tttccagagc gaatgagaag 2760
tctgttacaa tgccatctgg tctaagtcgg gagcagagaa gagcatgggc agcggagcag 2820
gcgcgcaaaa tccacaattg aatattgtct cattctctga gaccttcaac ctttattaca 2880
catccagata ttctgcaaaa acactcgata aaatcgatga tttcattgag catttgaaa 2940
aatacaatct cttgggcgat ccttaaaag gatatccagc ttggactggc aaagtatcgc 3000
catcgtggaa agtgcctgat cattacgaaa acaaagaagc tattgagaag tatgctagag 3060
ctaacaaatt atggcatgct catttaggcg atccggtttt taaagatacg tttcatggga 3120
aatacaaggt ttctgactgg gttattcatt tccagcggct gacaccgaac catataa    3177
```

```
          SpnI
atcctctagag tcgacctgca ggcatgctca aggcctgaca acccgtgtcgt ttttcgccaa   60
ctcctgcgag gtaacctcga acatgcgctg taagtttggcg tagctgtcct gccacgcttn  120
gctgctgttg ttcgtagtgc ctctgtaagc tctctaatgc gctcagaagc tgctgctcca  180
tttcggtcat gaatctcttc accctgatag ataaaaccgc ccagaatcga ttcctgtggcg  240
tctgatgagg ttatttggcg ctgtactttga tgacctgacg atgttgagcg ttcttgtact  300
cgtcgatctt cttcgcccc tgcggaagga tcaggtaata cacgctcttg ttcttggaat  360
cgtgaattat cgatacgccg gctccggtct ggctctttaa gtcctgcagg atctggctct  420
gctcgctgat ttcgttctgg cgttcgacca cgatagtccc gagataccaa gctactccaa  480
tcaatatcgc aaacaggatc ccacttaatg ccaggctgta cagccatgtc attccgacta  540
agcggtgtat ctgttttagc tggctgtcgt tctcttcttg gatagcggtc tgtatgttcc  600
ctgagcttaa tttcaaggcc tcggtgatac gtttctcgtg cttctcgaaa tgcgttcgcg  660
acgctcgttg cggtagtctt ggcttgctgn cttcgatttg ctctcgaact cccgcgctaa  720
atttaaaatc tcgctcatac agcactcctt ttaagcgaat attcgggcca cctgccgat  780
cagcaatact gatactggat ttggtttccc gtacgaccga caatccggca tcggtaaggt  840
gggaaatcac cccttttacga tccgtaattt ctccctgctc aatcaagctg attagccctt  900
tggtaatggc ttccgctgcc tgctgttttgt tgcgaggaag gtcattagag ggggttaatg  960
ctcggcgatt agcagggtca ttcgggtcgc gtaacccaag ccggtcattg gtgagggttt 1020
gccatgcgtt aacacgaggc cggtcagccc gatcaaagta aggttgtagc cgttttccgc 1080
tctgcaattc gatgttcggg ataacaaaat tcaattcaag acgcccttgg tcctgatgtt 1140
gaacccagag gcaggcatac tggtctttat ctagaccggt catcaatgtc tgctcccatt 1200
```

FIG. 4(b)

```
catccatcaa  tcgctgcttt  tcgccttcgg  gtaaatcact  ctcctgaaaa  gagagcacgc  1260
cagaggtata  agttcgggca  aattcgcagn  catcaatcag  ctctttgacg  tgctcagggt  1320
taccccgtaa  caccgtcgct  tgttcgcgct  gacgatcagg  gcccagaagg  taatcgacag  1380
gaccactccc  gccaccggca  ccacgaccat  gaatccttaa  cgatcacgat  gttgctccag  1440
cagttcggca  agatgttggt  caatgctatt  gagcaccgct  aacaacgaca  cccgttcttg  1500
cggcggtaag  ccatgctgat  tcaagtaacg  ggctatttga  ttgaggttat  taccgatccc  1560
gctgacctga  cgtaacaagg  tcggtctac   ggtaaggtta  gcggacgacg  cccgagctgt  1620
acgcgattcg  cctaagccaa  cggctcgtaa  ccactcggcc  aaatgcttac  ggtcacagcg  1680
ttcaagtagc  cgctgatgct  ccgcttcggt  gagtctgatt  ttgatctctt  tggtgcgctt  1740
ttccatgaga  atccgctgag  aaagtttcgc  acccaaagtg  cgaattttcg  cagtggatgc  1800
aaggggtttc  gggggcggc   gagcccccctg  aaacagtcac  agacggcacc  tcgaagaggg  1860
gacgctgtgt  gtactgrctt  agtacagcat  ctatcgtaca  tcgaggtcgc  atcacgcaca  1920
aacaaaaagc  cccgcaaaag  cagggctgtt  atctgatata  ggttgttttg  tctcacacgg  1980
cagcggaaga  ggaatccgaa  gtggtactgg  tagtagtatt  ggatgctgct  gacgatattt  2040
tccgctttga  cccaaggctt  aaataatcaa  tgcctgtaat  caacgatctc  aatacgcctt  2100
cggataccat  agcgataaac  gtatcttgct  ggttatggct  tgcgatgcaa  atcgtagcat  2160
caccttttt   atactttaaa  acacctgcta  aatatccatt  ttcatctaga  acactcttaa  2220
gatgttcatt  tgttattgtt  tgtagcgttt  gctttgtttc  gcttcgagca  tacgccttag  2280
ctagcttccg  agaaaaagca  tccgcatcat  gactatcttt  atttactcgc  tcaataaatt  2340
tgcttaagtc  aacaaatccc  ttaaaacgag  tggacatatt  gttaacaaaa  tcagtggcag  2400
```

FIG. 4(c)

```
catttttat ccatgcttta tagccaaaaa aacgctcgaa aacatttttgg tcgtagataa 2460
ataccgtatc gccagcaaaa acaagagatg ccttaccatc aatagaaatc atatcttgat 2520
ctactcgaga tagttccttt ttgctaaacc cataaaaatt atttttcttt cttgataagt 2580
tttgaactgg atattgcttc ttgtatatgg ttatacaatt gtcgtcatta ttcttactca 2640
aaacgaaaat gattgagtca acttttgata ttagatccac actgtcaaaa tcaacaattg 2700
ggatatttc attgccatca ccaccaaacc cagcatcaaa cacaatgcca gtcagaaact 2760
tcatttgctc attatcatac tgctcagcat catttaaaaa tgaaatggtg ttggtgcggt 2820
cacttagtgt attaacatct gatactatca caacccgatt ttctaaatca gatatagttt 2880
tcttttatcac attatcaata atggactgtt ttagctcact gtcatttta aggatggcaa 2940
tttttatagct aaaagagtcc ttagcaccg ctttaccttt atttttaaag ttaaagtaag 3000
tgtgcaatgt aacatcgtta atatcacatt caaaatgctt atacagttct aaaagctctt 3060
gtgcttttttc ttcattatgc tccaaagcat caagatcta aggcatcgtc actcatcatc 3120
attcctctat gatttttttc gcgaacgtta aataatcatc atgattata actctgataa 3180
aatcatttc ttttattaaa tctttagata aaactatcaa actcaccgtc ttgcgttttt 3240
tcccttccat tagctaccac actgtaagta atcttataga cagaaacatt aaataatgac 3300
aatgtttggt tgcagtgaat tctttttgtt ttgatgtgca aaaaaccgac gataatcaaa 3360
acaaacaaaa aattaactat atttgatggt ttgcttaaat cagtaaagac caacggcatt 3420
atgtacgttg ataaaaaaga aagatactca ccggattctt tttttacatga aacgacctttt 3480
aactttcttg acaccgcacc gggtctaag tttttcaaaa cccatcgata ccaaatgtat 3540
gtataagaac aagttaaaat caaagccccg cagatcactg acctcaatac agaaaatgtt 3600
```

FIG. 4(d)

```
aatctgctat ttgaatagtc gagtacgcat tgaaattttc catccgcgcc agaacacgaa 3660
gacatggcct tatctaaaac agaccatacg ttatcaatac cagaaaaata tattgttatc 3720
ggtataaaat aaaaacaaca ttgataagag atacattcta atttcattt ttgtaaaatt 3780
tcctgtacca cgttgatcta cttattccta aagaaatcca ttctccatct ctaactttcg 3840
gccttccacc accagagctt tttttccac gttgacgctg aatttcagaa gtatgtgttt 3900
gtttaacata ctcttcaaag ccaagctctg taaggttctt acttgtccac ttagccacac 3960
ttttagcaat tcccatgact tcgttctgt ctaaaggtgc ggagaactgc aggttgtagg 4020
ctttagcgcg ttcaatgcag gcttgtagcc attggtcata ctgcggccag ccttggcgga 4080
tagcgcggta agcccacttg cgggttttat cgaagagggt gcagttacgg cctaaaccgt 4140
agtccggcag gatttcgcgg tcattggctg cgccaaggtc cgcaaccgt gctaaccagt 4200
caagggtata gagctctggc tgccagacgg tgatctgcca gtgcaggtgg ttcggattct 4260
tgcaaattag ccctgaatac cccgcatctg cgcccaattt ttacgcagc gcattcctga 4320
tggcgcggc gtatttaagg ggggcagctc gaccatccgg cgcggtacgt accgcgtat 4380
gcaaggcata caacaggtga gcatgtccgt tctcggggtt tttgatggtg agtgtgggcg 4440
caggtgcccc cagatcggcc caatcaatcg cggctccggc tctgtccacg tcaaagcaaa 4500
gccagtacat ggcgtgaggc tgattaaact ggatgtattt tgcgaggaga gcacgctctt 4560
taccggcaat gcgaacacca aactgtaaat catcggagaa gtacgcttg tggggtaacc 4620
ggtcgttaaa aagcgttaaa gcctgattat cagccttatg cagcctagcc gcggggctgt 4680
tgttttgcac gctgcatgtg ctaatatcct ttctagtttt cgacctagcc ctgaatgtca 4740
tgtccgctcg ccaaagtaga gcatgatttc ggggctttgt tttttctgcc actaagttac 4800
```

FIG. 4(e)

```
acctcaacaa cggtttttgt catccccgac aatccgttat tcctgcttgt tctcgcacgg 4860
ctttacgctc atactacttc ttgtagatac acttgtcact acatcaagag gtgagatgat 4920
ggccacgatt aatattcgga tcgatgacga gctgaaaagc cgctcttatg ccgcactgga 4980
aaagctgggc gtaacgccgt ccgaggttct gcgccaaaca ctggaatatg tggcccaaag 5040
cggacgtttg ccgttccagc aggtttttgct gatgccgatt tgatggctat 5100
cgttcgggat cgtctggaaa acccacaggc ggggcgtaaa ggtgtcactg gatgagctat 5160
aacctttgaat ttgatcccg agccctgaag aaggaatggc gcaagctcgg ggatgatgtc 5220
cgtctgcagt tcaagaaaaa actcgagcag gttctacaac accccgcgga tcgataaaaa 5280
tcgcctgcga gagcgcatg actgctacaa aatcaagctc cgtgcatccg gttatcgctt 5340
nggtctatca ggttcgcgat caaaccatta cggtattcgt ggtggcggtc ggtaagggcn 5400
gagcgttctg ccgcttacga tgcggcccga taaacgctta ccgtcaccgc 5460
gagaataccg gcttggctaa ttgctccaag cggcgcagtg ttgtgtttaa 5520
gctctcgact tcgtgcgcca agccggtgac tt 5552
```

FIG. 5

BACTERIAL PLASMIDS

This is a division of Application Ser. No. 09/402,039, filed Dec. 23, 1999, abandoned, which is a §371 U.S. national phase application of PCT/EP98/01720 filed Apr. 1, 1998.

BACKGROUND OF THE INVENTION

The invention relates to bacterial plasmids.

FIELD OF THE INVENTION

Plasmids are small, extra-chromosomal, mostly circular and independently replicating DNA molecules, which occur in nearly all bacteria and also in some eukaryons as well as in the mitochondria. The size of the plasmids vary between approximately 1.5 to 300 kb.

As a rule bacterial plasmids are circular, covalently closed and supercoiled. They often carry resistance genes against antibiotics or heavy metals, genes for the metabolization of a typical substrates or genes for a number of specie-specific characteristics, such as metabolic properties or virulence factors. Some plasmids can be transferred from one cell into another. Because the pathogenity of bacteria is determined according to present views, partly also by the properties of the plasmids, there exists increasingly a greater interest to clarify the properties of the plasmid DNA.

It is known of the family of entereobacteriacea, to whom 14 main varieties and 6 further varieties belong, that family members can develop different properties. Typical family members are, for example, Escherichia, Salmonella and Klebsiella. *Escherichia coli* (*E. coli*) is the classic model for the study of bacterial genetics. By discovering and characterizing different virulence factors of *E. coli*, strains of this species were generally found to exhibit differences in human and animal pathogenicities. These differences may be extreme, ranging from avirulence to high grade virulence, such as in the case of the recently spreading variant known as "EHEC". Thus, a number of virulence factors have been described for extra-intestinal as well as for intestinal *E. coli* strains, which have been partially characterized. The serovariety 06:K5 virulence factors, such, as for example, haemolycin and P-fimbrial adhesion are known to be associated with pathogenic *E. coli*, while apathogenic representations of this sero-variety typically lack these virulence factors.

As in rule virulence genes are found at enterobacteria on large plasmids (approximately 60 kb). There are also enterobacteria with small, so-called cryptic plasmids, whose function hitherto could not be reliably determined.

SUMMARY OF THE INVENTION

Because it is known that *E. coli* virulence factors are at least partly also present in genes of the plasmids, there exists a need for further, data regarding the detection and characterization of plasmids in enterobacteria, especially Escherichia. Such information will improve, for example, diagnostic and therapeutic treatment of enterobacterial infections. Such plasmids, or their bacterial carriers, or corresponding synthethized DNA can be applied medicinally in therapeutics or for prophylaxis of Enterobacterial infections, as well as for nutritional, physiological or probiotic purposes in microbiological analysis or diagnostics testing of such infections. Furthermore, plasmids, especially those of *E. coli*, are known expression vectors used in genetic engineering, increasing the interest in and learning more about the properties of such plasmids.

DETAILED DESCRIPTION OF THE INVENTION

Molecular genetic investigations with the *E. coli* strain DSM 6601 were performed for this purpose. The DNA sequences obtained from this strain were examined with the help of data bank programs of DNA sequence analysis and compared with already existing DNA sequences of other bacteria.

The strain DSM 6601 contains two small plasmids with a size of 3177 or 5552 bp, which are described respectively as pMUT1 or pMUT2.

Figure 1A:
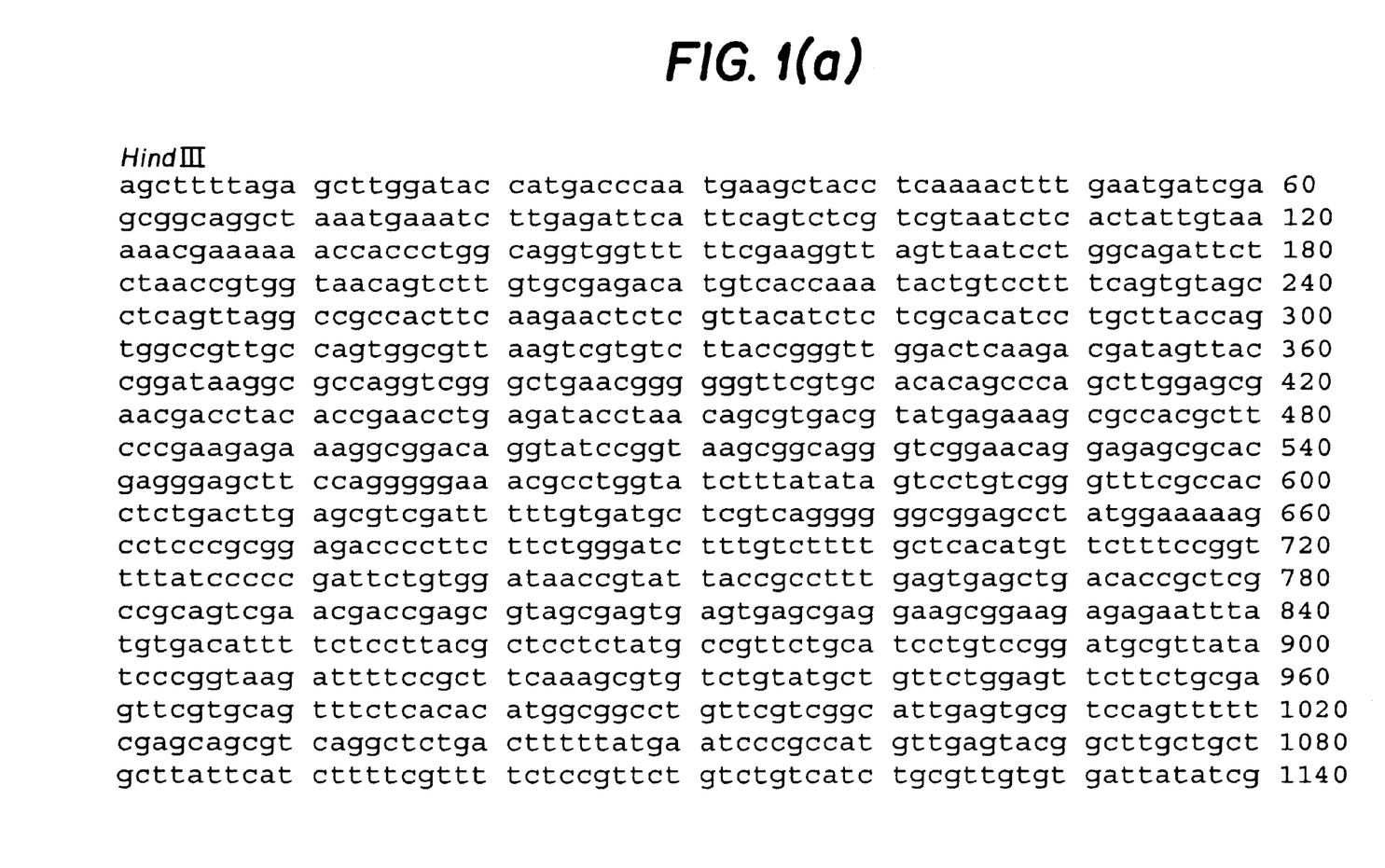
FIG. 1 depicts a representation of the nucleoaide sequence of the approximately 3 kb sized plasmid pMUT1 of the strain DSM 6601 (SEQ ID NO.:1)
Figure 1B:
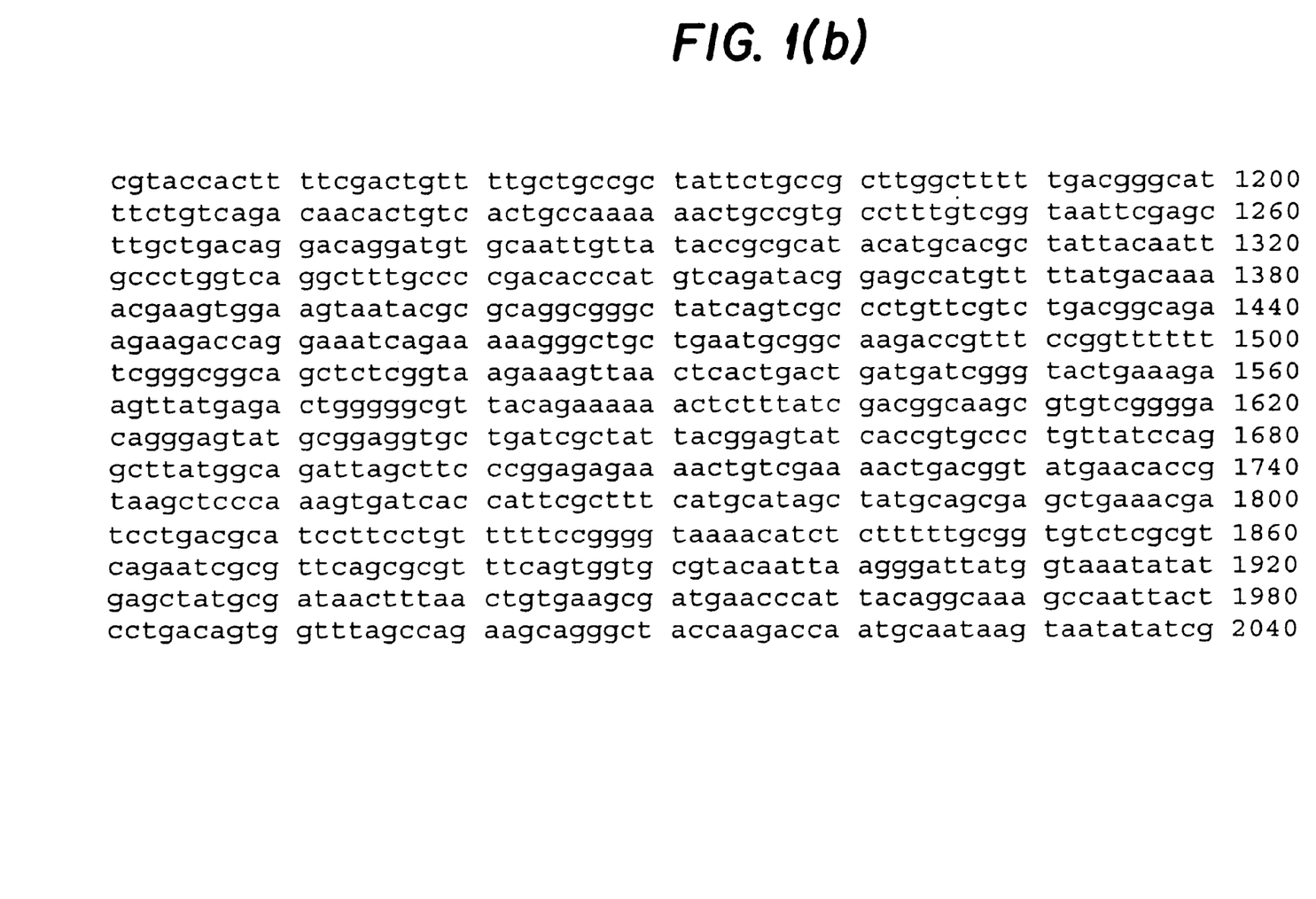
Figure 1C:
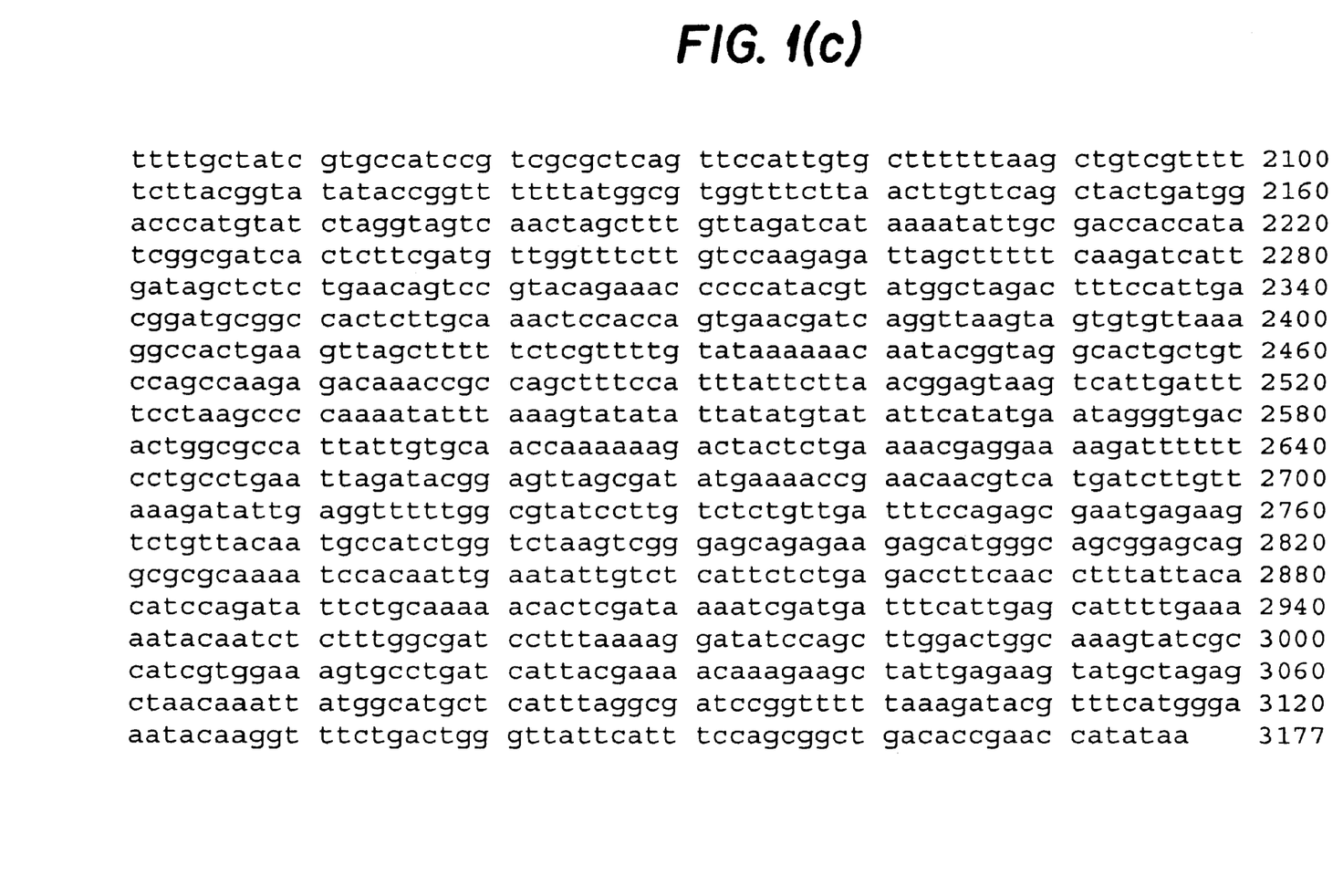

The DNA of the smaller plasmids pMUT1 were subcloned as a linear fragment into the vector pUC18, after restrictional fission with the enzyme HindIII, the DNA sequence was subsequently determined. This is evident from the enclosed FIG. 1 (SEQ ID NO.: 1). The resulting DNA sequence was examined by means of a homologous comparison with the GenEMBL data bank; the results of this comparison are given in FIG. 2.

Figure 2:
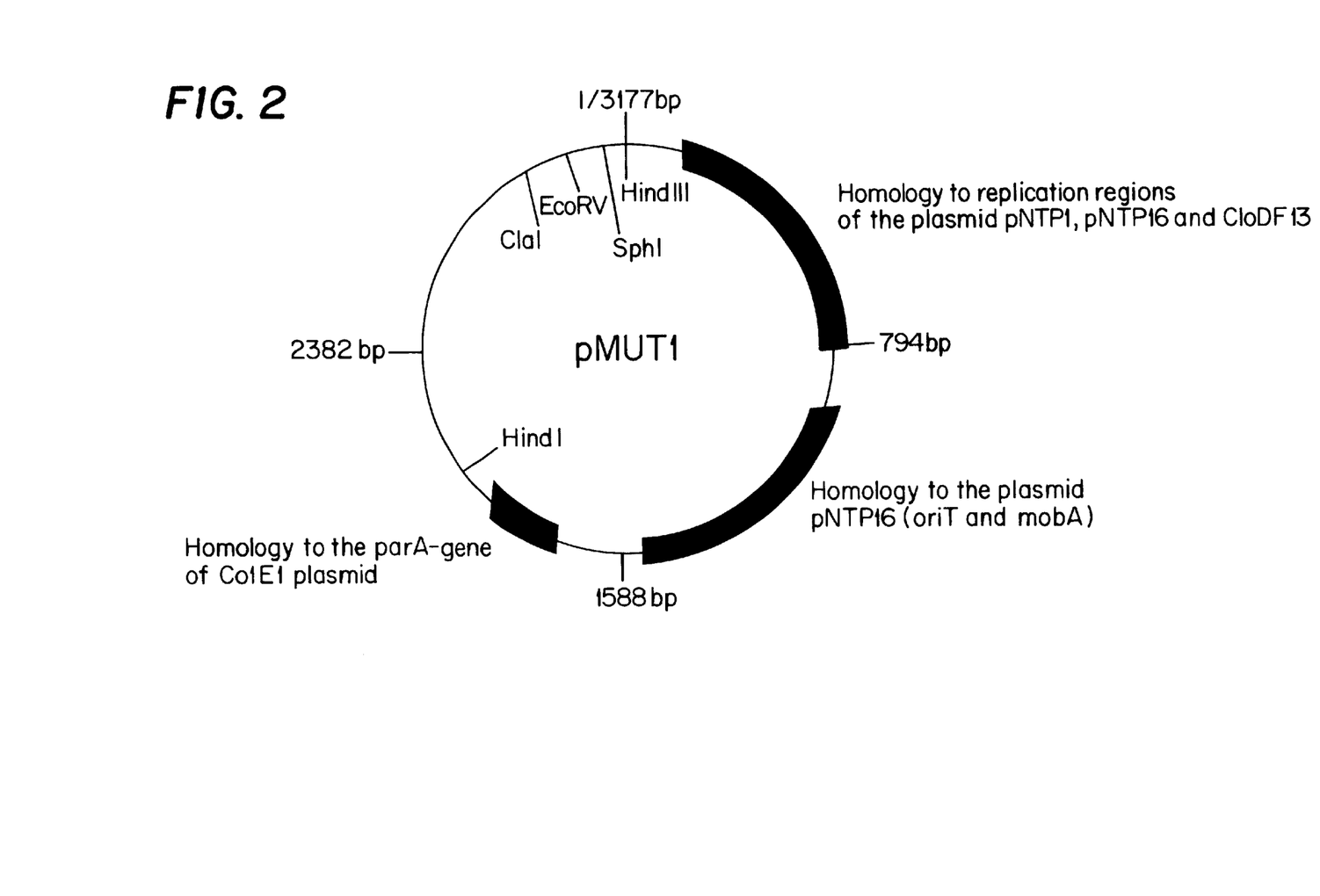
FIG. 2 depicts a restriction map of the plasmid pMUT1, wherein black bars symbolize the DNA sequence homologies found to the DNA sequence of plasmids of other enterobacteria, and the position of the relevant restriction intersections are given.

For this comparison the HindIII intersection was fixed as Position 1. From the position 200 to 800 bp the DNA of the plasmid pMUT1 exhibits significant homologies to different reduplication starting positions (origins of replication) of other enterobacterial plasmids, especially to the plasmids NTP1, NTP16 and CloDF13. In the region of position 950 bp, a 570 bp sized homology starts to the plasmid NTP16, which originally was isolated from Salmonella Typhimurium. This homology contains the mobA-gene, which is necessary for the mobilizability of the plasmids NTP16 as well as for an origin of transfer (oriT). Furthermore, significant homologies to the gene parA and cer were found from position 1790 up to 1920 bp, which are significant for the stability and the continuous transfer and distribution of plasmid molecules during cell division. For the remaining DNA regions, no significant homology could be identified.

Figure 3A:
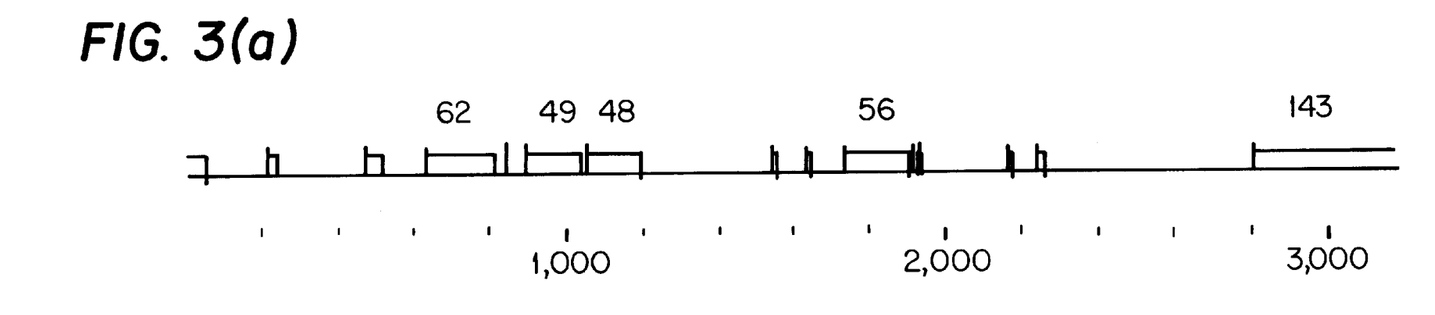
FIG. 3a is a representation of the plasmid pMUT1found in open reading frames, the sizes of which are indicated.

Furthermore, the DNA sequence of the plasmid pMUT1 were transcribed into an amino acid sequence and analyzed for the existence of open reading frames. Six different reading frame possibilities were investigated. In total, 5 open reading frames with a size of 143, 62, 56, 49 and 48 amino acids could be found. A graphic representation of the analysis is given in FIG. 3.

Figure 5:
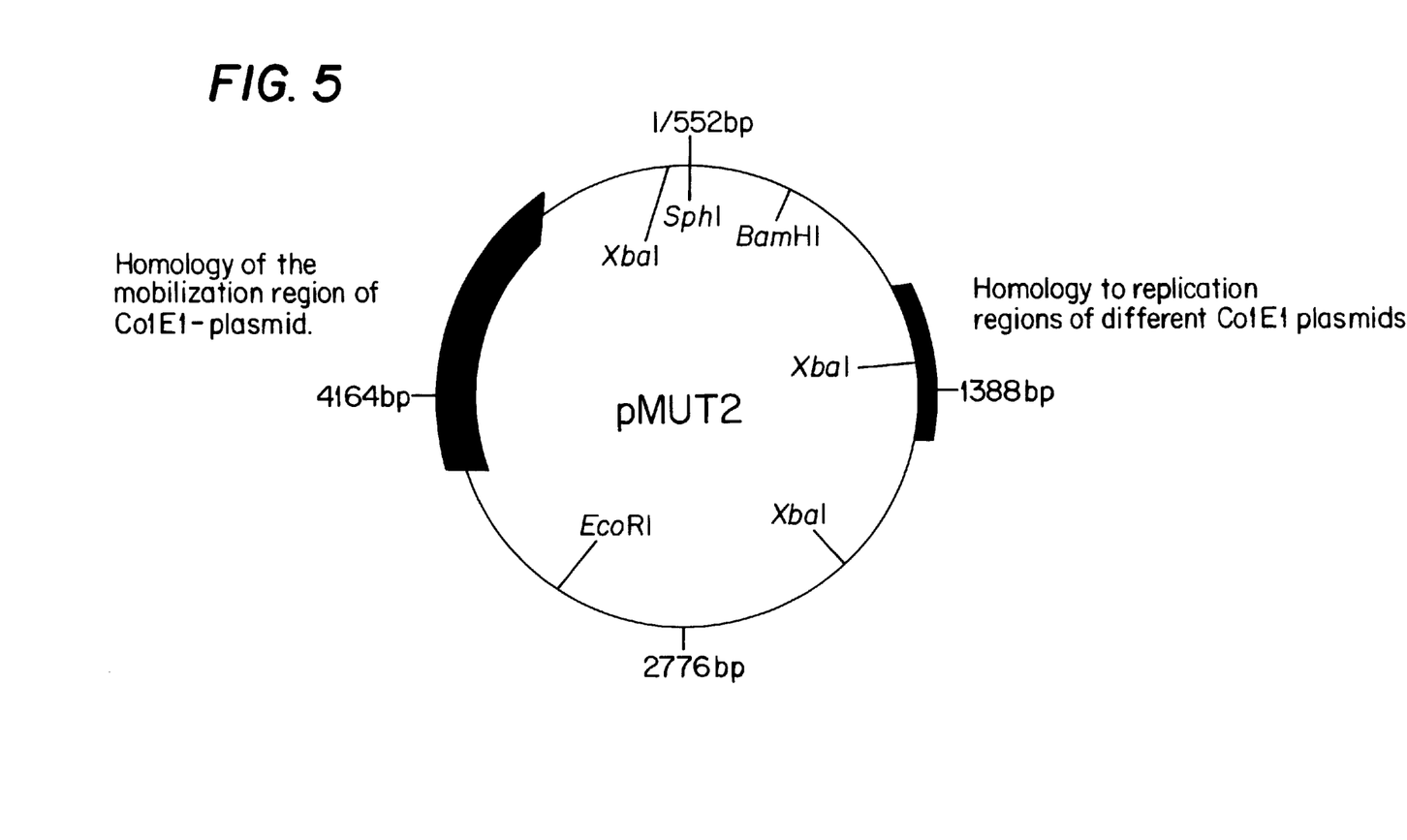
FIG. 5 depicts a restriction map of the plasmid pMUT2, wherein black bars symbolize the DNA sequence homologies found to the DNA sequence of plasmids of other enterobacteria, and the position of the relevant restriction intersections are given.

The DNA of the larger plasmid pMUT2 were likewise sub-cloned after linearization with the restriction enzyme Sphl into the vector pUC18 and subsequently were sequenced completely. The DNA sequence is given in FIG. 4 (SEQ ID NO.: 2). The DNA sequence obtained in this manner was investigated with the help of the GeneEMBL data bank program for homologies with known DNA sequences. The result is graphically represented in FIG. 5. The DNA of the plasmid pMUT2 exhibits significant homologies to the replication region of different ColE1 plasmids of *E. coli* in the position 890 up to 1660 bp. A further significant homology to CoE1 plasmids is found in the region of position 3800 up to 4950 bp. Here it concerns homologies for the mobilization region of ColE1 plasmids. In the area of position 3770 up to 4980 bp, homologies were found to a plasmid of the *Pasteurella haemolytica* strain A1. There are genes on this plasmid which encode for antimicrobial resistance proteins in Pasteurella. However, the homology stretches over the intergenetic region, so that it possibly also concerns sequences that are necessary for the mobility of the plasmids.

Two regions were identified, which exhibit significant homologies to other enterobacterial plasmids. These hemologous regions concerns the origin-of-replication-regions and mob-regions, which are necessary for the mobilizability of the plasmids. For pMUT2 no significant homology could be identified for the remaining DNA sections.

Figure 3B:
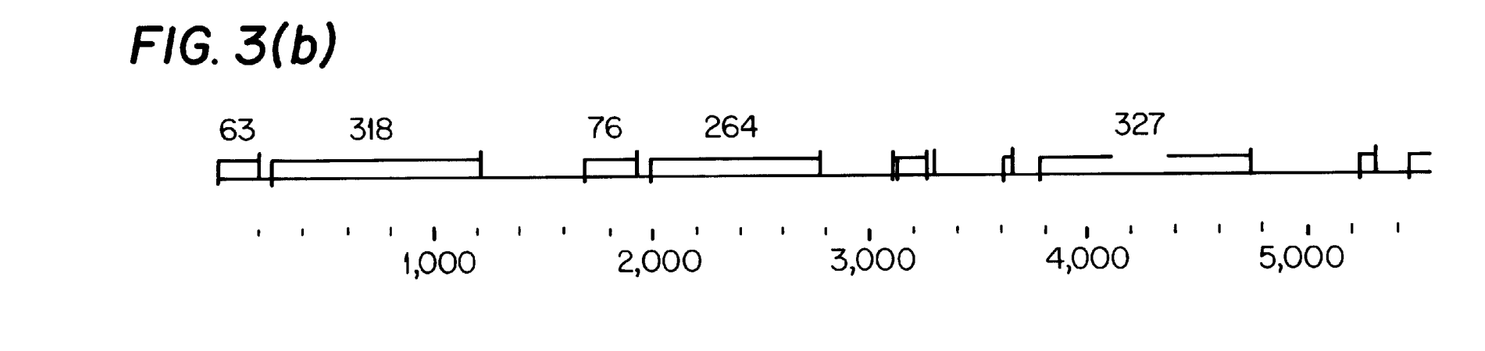
FIG. 3b is a representation of the plasmid pMUT2 found in open reading frames, the sizes of which are indicated.
Figure 4A:
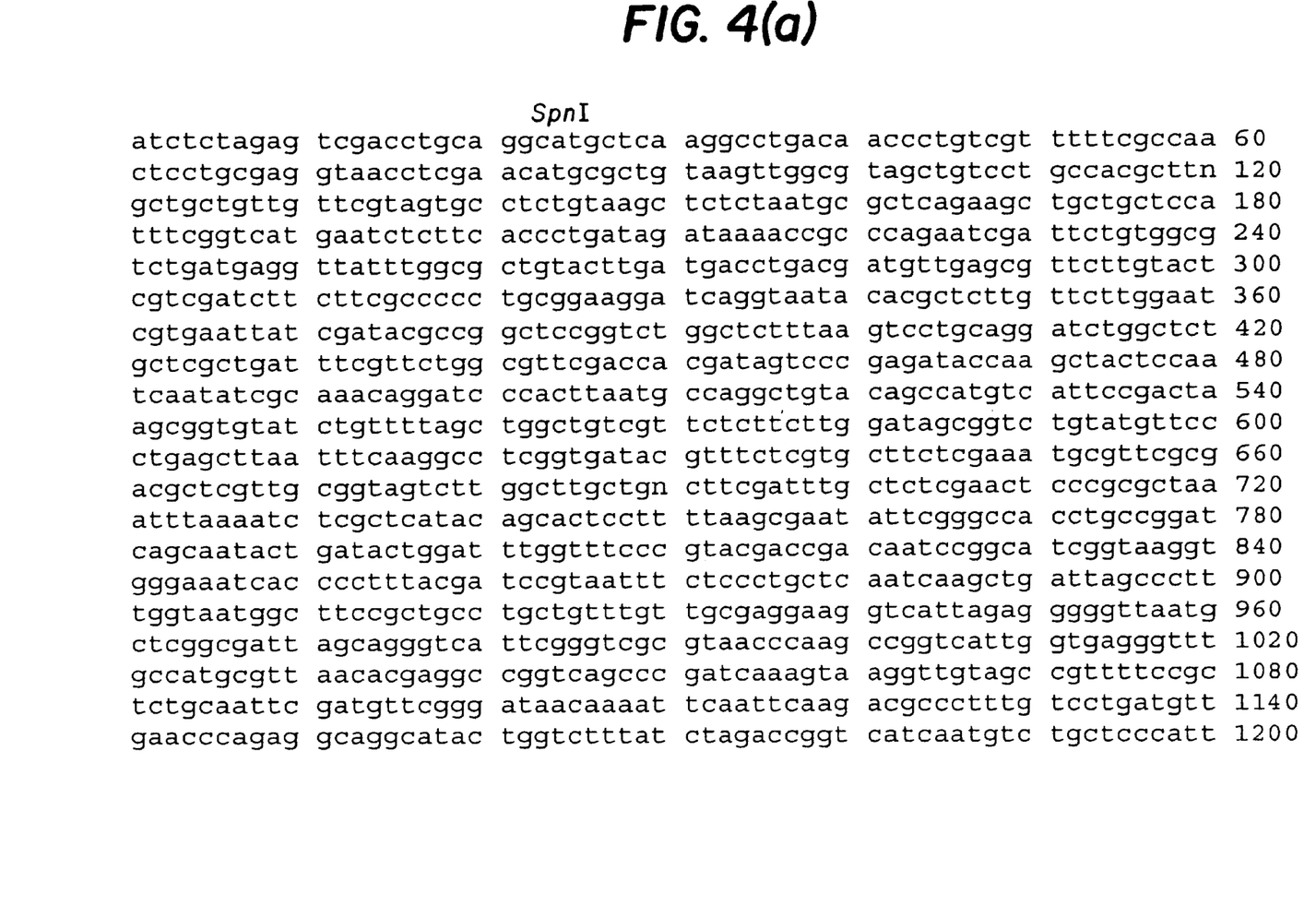
FIG. 4 is a representation of the nucleotide sequence of the approximately 5 kb sized plasmids pMUT2 of the strain DSM 6601 (SEQ ID NO.: 2)
Figure 4B:
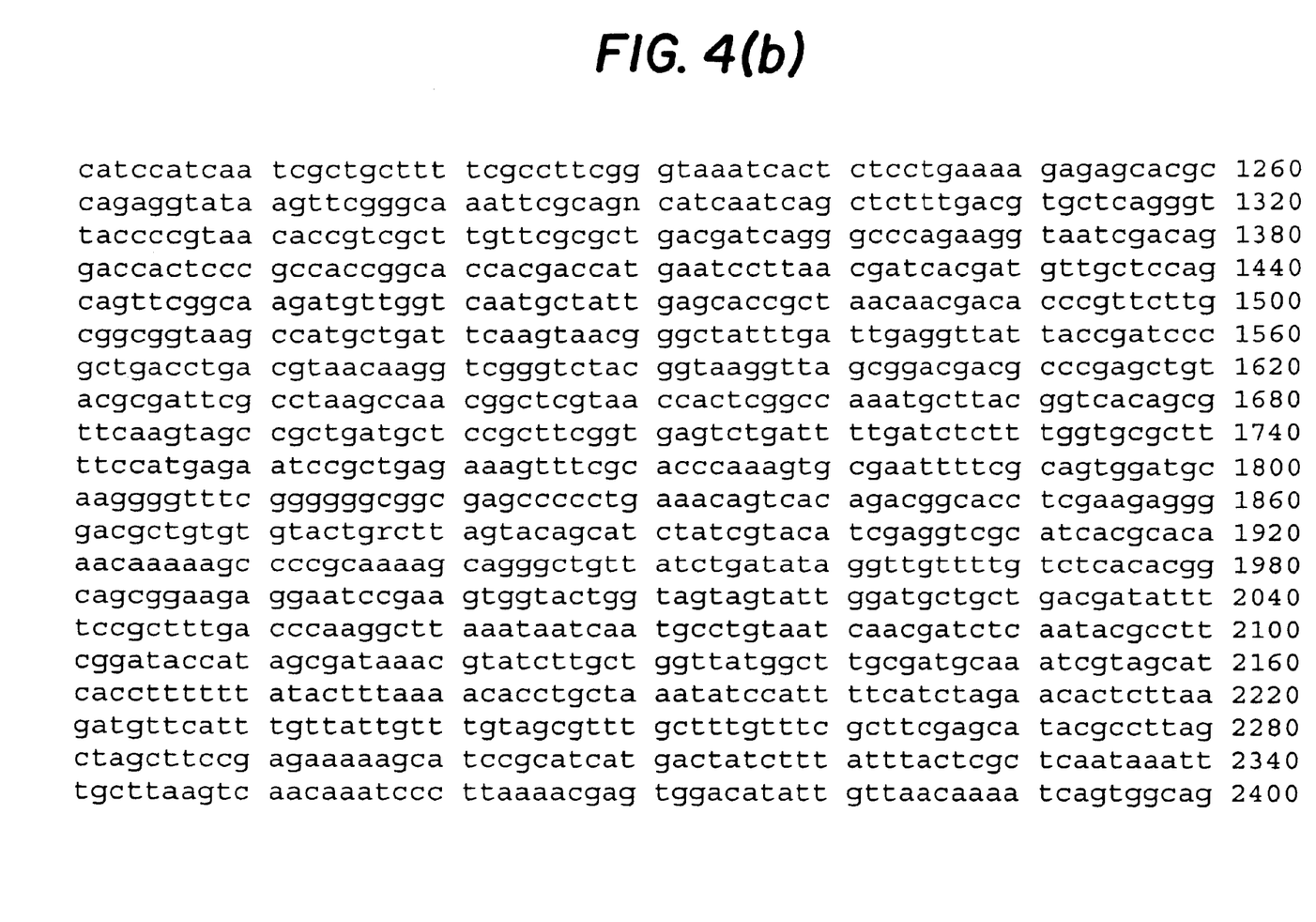
Figure 4C:
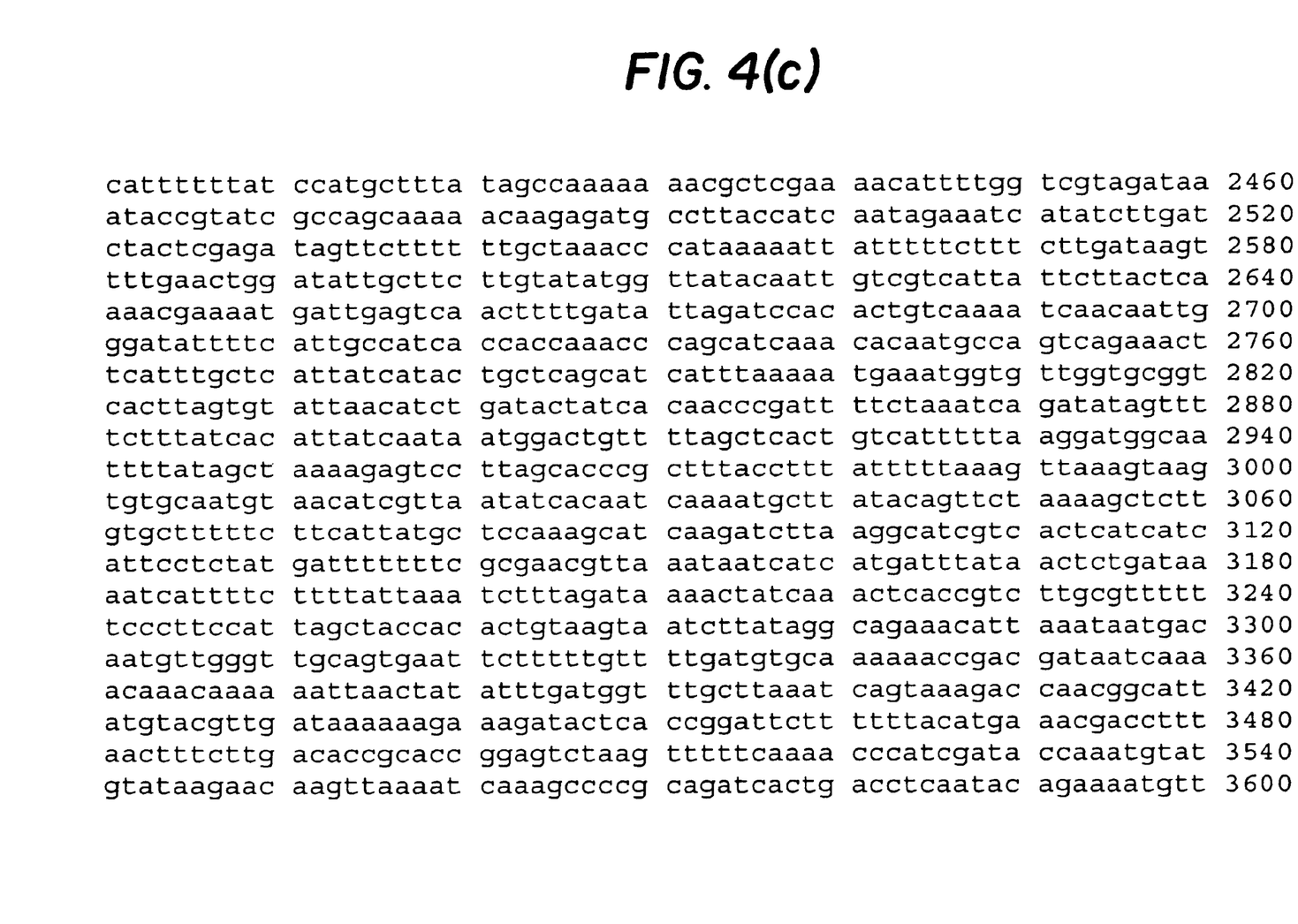
Figure 4D:
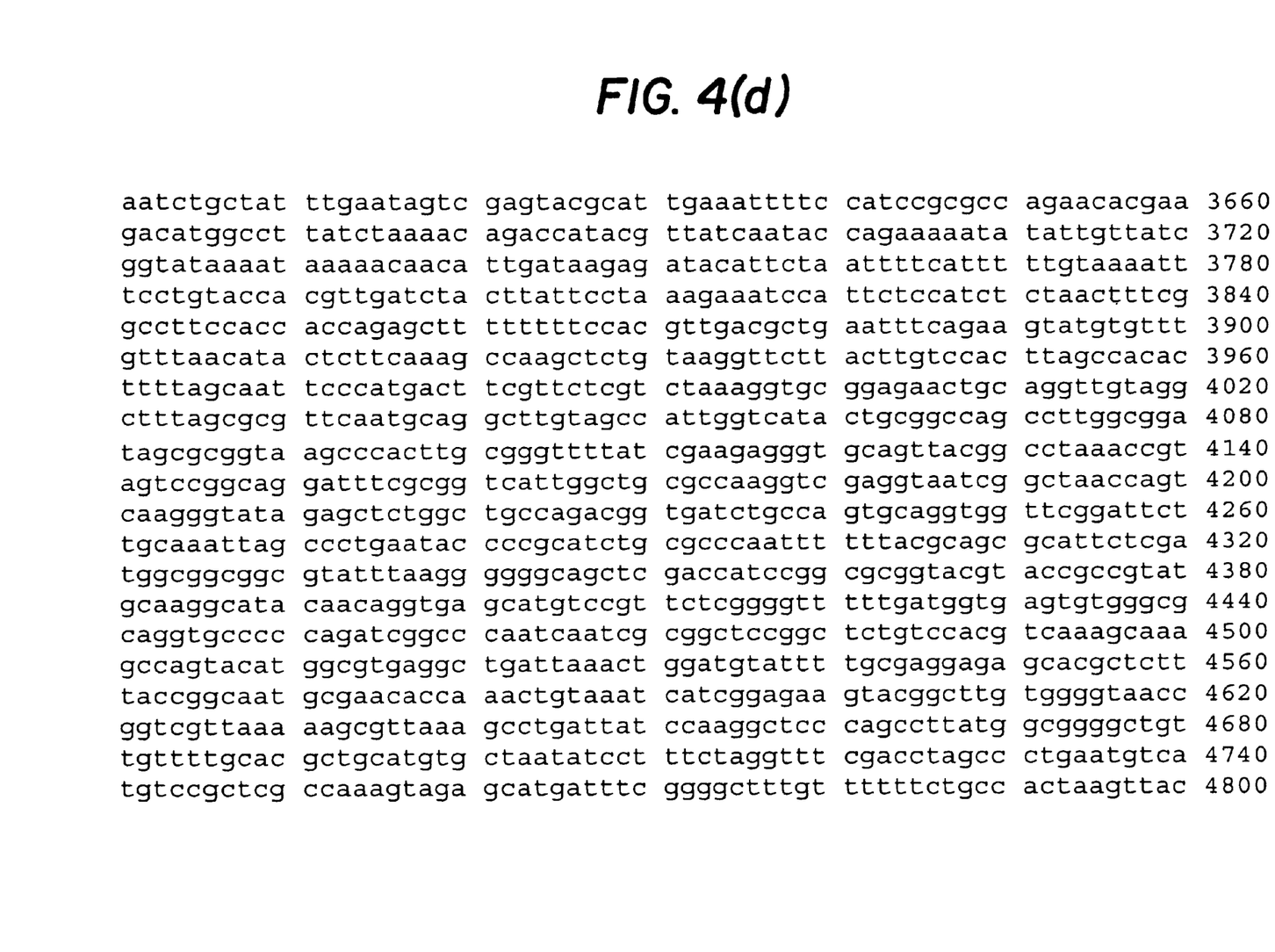
Figure 4E:
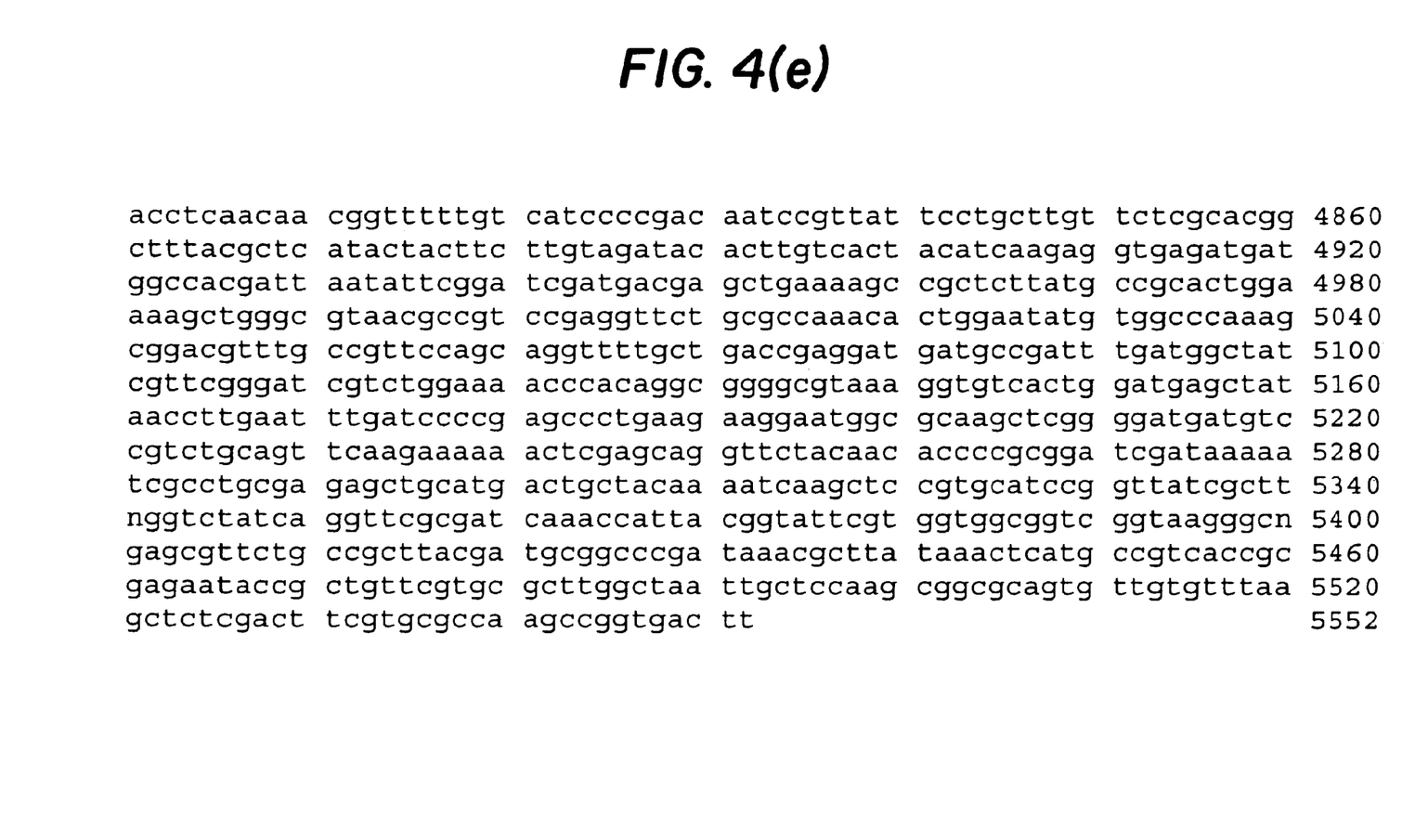

The DNA sequence of the plasmid pMUT2 was subsequently circumscribed into an amino acid sequence and analyzed for the existence of open reading frames. The results are graphically represented in FIG. 3. Five open reading frames with amino acid sequences in the order of 327, 318, 264, 76 and 63 amino acids were found.

The previously unknown plasmids pMUT1 and pMUT2, were not known heretofore to be present either alone or in combination in *E. coli* strains or other enterobacteria.

The occurrence of the plasmids may be related to the metabolic and medicinal and/or nutritional, physiological, or probiotic usable properties of the strain DSM 6601.

The investigation of the plasmids allows a more precise determination and analysis of enterobacteria, especially the Escherichia groups. Furthermore, these plasmids offer themselves as reliable expression vectors for genetic engineering.

The invention shall now be further explained by way of examples:

EXAMPLE 1

Plasmid Isolation.

The isolation of the plasmid DNA occurred according to the process of Birnboim et al. (Birnboim, A.C. und Doly, J. (1979) Nucl. Acids Res. 7:1513–1523 A rapid alkaline extraction procedure for screening recombinant plasmid DNA).

3 ml LB-medium were inoculated with a bacteria colony and agitated overnight at 37° C. This culture is centrifuged off in an Eppendorf vessel, the medium residue is removed by means of a pipette. The cell sediment is re-suspended with 100 µl of solution I (50 mM glucose; 10 mM EDTA, pH 8; 25 mM Tris-HCl, pH 8). After 5 minutes of incubation at room temperature 200 µl of solution II (0,2 N NaOH; 1% SDS) is added, mixed until clarification and the Eppendorf vessel is left on ice for a further 5 minutes. Then 150 µl of solution III (3 M Na-acetate, pH 4.8)is added thereto, agitated briefly until the chromosomal DNA precipitates flocculantly, and the sediment is left again on ice for 5 minutes. The precipitated chromosomal DNA and the cell residues are pelletized for 5 minutes in the centrifuge and the residue with the plasmid DNA is transferred to a new vessel. For the purification of the plasmid DNA, 50 µl phenol and 150 µl chloroform/isoamyl alcohol (24:1) are added and after brief agitation centrifuged off for 2 minutes. The aqueous phase is pipetted into a new vessel. The plasmid DNA is precipitated with 2 volumes ice-cold ethanol and centrifuged off for 10 minutes. The pellet is washed with 70% ethanol and dried in the Speedvac. The plasmid DNA is re-suspended in 20 µl $H_2O_{bidest}$ and preserved at −20° C.

EXAMPLE 2

DNA Sequencing

The DNA sequencing occurs according to the process of F. Sanger et al. (Sanger, F., Nicklen, S. and Coulson, A. R. (1977) Proc. Natl. Acad. Sci. USA 74:5463–5467 DNA sequencing with chain terminating inhibitors).

The DNA sequencing occurs with the T7-sequencing kit of the company Pharmacia LKB.

For the denaturization step 8 µl (1.5 up to 2 µg) plasmid DNA is mixed with 2 µl 2 N NaOH, briefly centrifuged off and incubated for 10 minutes at room temperature. The DNA is precipitated with 3 µl 3 M Na-acetate, pH 4.8 as well as 7 µl $H_2O_{bidest}$ and 60 µl ice-cold $ethanol_{absolute}$ for 15 minutes at −70° C. The precipitated DNA is centrifuged off for 10 minutes, washed with 70% ethanol and dried.

For the annealing reaction the denaturated DNA is suspended in 10 µl $H_2O_{bidest}$ and mixed with 2 µl annealing powder and 2 µl primer (40 ng). The sediment is incubated for 20 minutes at 37° C., so that a bonding of the primer to the template-DNA can occur. The reaction sediment is cooled down for 10 minutes at room temperature and then either immediately used for the labelling reaction or is frozen at −20° C. For the labelling reaction 3 µl labelling mixture, 1 µl [α-$P^{32}$]dATP and 2 µl T7-polymer (the T7-polymer was diluted 1:5 with enzyme dilution powder) are pipetted in the annealing reaction sediment and after briefly mixing are incubated for 5 minutes at room temperature. Meanwhile the already prepared sequencing mixture for the termination reaction (each 1 vessel with 2.5 µl 'G'-, 'A'-, 'T'- and 'C'-Mix "short") is preheated at 37° C. After completion of the labelling reaction 4 µl thereof is added to each of the four sequencing mixtures and briefly mixed by means of the pipette. The termination reactions are incubated for 5 minutes at 37° C. For the conclusion of the termination reaction 5 µl stop solution is added respectively. The sediments are now transferred into an incubator at 95° C., denaturized for 2 minutes and then placed on ice. Each 2.5 µl of the reactions are spread on a sequencing gel [25.2 g carbamide, 22 ml $H_2O_{bidest}$, 6 ml 10× TBE, 10 ml polyacryl amide (40%), 2 ml ammonium persulfate (16 mg/ml), 60 µl TEMED] in the sequence of a 'G', 'A', 'T', 'C'. The electrophoresis occurs at 40 Watt and 1500 Volt for 4.5 hours.

What is claimed is:

1. A plasmid comprising the DNA sequence defined by SEQ ID NO: 1.
2. A plasmId comprising the DNA sequence defined by SEQ lD NO.: 2.
3. An isolated DNA sequence comprising the nucleotide sequence defined by SEO ID NO.: 1.
4. An isolated DNA sequence comprising the nuclotide sequence defined by SEQ ID NO.: 2.
5. An expression vector comprising the plasmid according to claim 1 or claim 2.
6. An expression vector comprising the DNA sequence according to claim 3 or claim 4.

* * * * *

SEQUENCE LISTING

<160> NUMBER OF SEQ ID NOS: 2

<210> SEQ ID NO 1
<211> LENGTH: 3177
<212> TYPE: DNA
<213> ORGANISM: Escherichia coli

<400> SEQUENCE: 1

| | | | | | |
|---|---|---|---|---|---|
| agcttttaga | gcttggatac | catgacccaa | tgaagctacc | tcaaaacttt gaatgatcga | 60 |
| gcggcaggct | aaatgaaatc | ttgagattca | ttcagtctcg | tcgtaatctc actattgtaa | 120 |
| aaacgaaaaa | accaccctgg | caggtggttt | ttcgaaggtt | agttaatcct ggcagattct | 180 |
| ctaaccgtgg | taacagtctt | gtgcgagaca | tgtcaccaaa | tactgtcctt tcagtgtagc | 240 |
| ctcagttagg | ccgccacttc | aagaactctc | gttacatctc | tcgcacatcc tgcttaccag | 300 |
| tggccgttgc | cagtggcgtt | aagtcgtgtc | ttaccgggtt | ggactcaaga cgatagttac | 360 |
| cggataaggc | gccaggtcgg | gctgaacggg | gggttcgtgc | acacagccca gcttggagcg | 420 |
| aacgacctac | accgaacctg | agatacctaa | cagcgtgacg | tatgagaaag cgccacgctt | 480 |
| cccgaagaga | aggcggaca | ggtatccggt | aagcggcagg | gtcggaacag gagagcgcac | 540 |
| gagggagctt | ccaggggaa | acgcctggta | tctttatata | gtcctgtcgg gtttcgccac | 600 |
| ctctgacttg | agcgtcgatt | tttgtgatgc | tcgtcagggg | ggcggagcct atggaaaaag | 660 |
| cctcccgcgg | agacccttc | ttctgggatc | tttgtctttt | gctcacatgt tctttccggt | 720 |
| tttatccccc | gattctgtgg | ataaccgtat | taccgccttt | gagtgagctg acaccgctcg | 780 |
| ccgcagtcga | acgaccgagc | gtagcgagtg | agtgagcgag | gaagcggaag agagaattta | 840 |
| tgtgacattt | tctccttacg | ctcctctatg | ccgttctgca | tcctgtccgg atgcgttata | 900 |
| tcccggtaag | attttccgct | tcaaagcgtg | tctgtatgct | gttctggagt tcttctgcga | 960 |
| gttcgtgcag | tttctcacac | atggcggcct | gttcgtcggc | attgagtgcg tccagttttt | 1020 |
| cgagcagcgt | caggctctga | ctttttatga | atcccgccat | gttgagtacg gcttgctgct | 1080 |
| gcttattcat | cttttcgttt | tctccgttct | gtctgtcatc | tgcgttgtgt gattatatcg | 1140 |
| cgtaccactt | ttcgactgtt | ttgctgccgc | tattctgccg | cttggctttt tgacgggcat | 1200 |
| ttctgtcaga | caacactgtc | actgccaaaa | aactgccgtg | cctttgtcgg taattcgagc | 1260 |
| ttgctgacag | gacaggatgt | gcaattgtta | taccgcgcat | acatgcacgc tattacaatt | 1320 |
| gccctggtca | ggctttgccc | cgacacccat | gtcagatacg | gagccatgtt ttatgacaaa | 1380 |
| acgaagtgga | agtaatacgc | gcaggcgggc | tatcagtcgc | cctgttcgtc tgacggcaga | 1440 |
| agaagaccag | gaaatcagaa | aaagggctgc | tgaatgcggc | aagaccgttt ccggtttttt | 1500 |
| tcgggcggca | gctctcggta | agaaagttaa | ctcactgact | gatgatcggg tactgaaaga | 1560 |
| agttatgaga | ctgggggcgt | tacagaaaaa | actctttatc | gacggcaagc gtgtcgggga | 1620 |
| cagggagtat | gcggaggtgc | tgatcgctat | tacggagtat | caccgtgccc tgttatccag | 1680 |
| gcttatggca | gattagcttc | ccggagagaa | aactgtcgaa | actgacggt atgaacaccg | 1740 |
| taagctccca | aagtgatcac | cattcgcttt | catgcatagc | tatgcagcga gctgaaacga | 1800 |
| tcctgacgca | tccttcctgt | ttttccgggg | taaaacatct | cttttttgcgg tgtctcgcgt | 1860 |
| cagaatcgcg | ttcagcgcgt | ttcagtggtg | cgtacaatta | agggattatg gtaaatatat | 1920 |
| gagctatgcg | ataactttaa | ctgtgaagcg | atgaacccat | tacaggcaaa gccaattact | 1980 |
| cctgacagtg | gtttagccag | aagcagggct | accaagacca | atgcaataag taatatatcg | 2040 |

-continued

```
ttttgctatc gtgccatccg tcgcgctcag ttccattgtg cttttttaag ctgtcgtttt    2100
tcttacggta tataccggtt ttttatggcg tggtttctta acttgttcag ctactgatgg    2160
acccatgtat ctaggtagtc aactagcttt gttagatcat aaaatattgc gaccaccata    2220
tcggcgatca ctcttcgatg ttggtttctt gtccaagaga ttagcttttt caagatcatt    2280
gatagctctc tgaacagtcc gtacagaaac ccccatacgt atggctagac tttccattga    2340
cggatgcggc cactcttgca aactccacca gtgaacgatc aggttaagta gtgtgttaaa    2400
ggccactgaa gttagctttt tctcgttttg tataaaaaac aatacggtag cactgctgt     2460 ccagccaaga gacaaaccgc cagctttcca tttattctta acggagtaag tcattgattt    2520
tcctaagccc caaatatttt aaagtatata ttatatgtat attcatatga ataggtgac    2580 actggcgcca ttattgtgca accaaaaaag actactctga aaacgaggaa agatttttt    2640 cctgcctgaa ttagatacgg agttagcgat atgaaaaccg aacaacgtca tgatcttgtt    2700
aaagatattg aggttttttgg cgtatccttg tctctgttga tttccagagc gaatgagaag    2760
tctgttacaa tgccatctgg tctaagtcgg gagcagagaa gagcatgggc agcggagcag    2820
gcgcgcaaaa tccacaattg aatattgtct cattctctga gaccttcaac ctttattaca    2880
catccagata ttctgcaaaa acactcgata aaatcgatga tttcattgag cattttgaaa    2940
aatacaatct ctttggcgat cctttaaaag gatatccagc ttggactggc aaagtatcgc    3000
catcgtggaa agtgcctgat cattacgaaa acaaagaagc tattgagaag tatgctagag    3060
ctaacaaatt atggcatgct catttaggcg atccggtttt taaagatacg tttcatggga    3120
aatacaaggt ttctgactgg gttattcatt ccagcggct gacaccgaac catataa       3177
```

<210> SEQ ID NO 2
<211> LENGTH: 5552
<212> TYPE: DNA
<213> ORGANISM: Escherichia coli
<220> FEATURE:
<221> NAME/KEY: modified_base
<222> LOCATION: (120)
<223> OTHER INFORMATION: A, T, C or G
<221> NAME/KEY: modified_base
<222> LOCATION: (661)
<223> OTHER INFORMATION: A, T, C or G
<221> NAME/KEY: modified_base
<222> LOCATION: (1290)
<223> OTHER INFORMATION: A, T, C or G
<221> NAME/KEY: modified_base
<222> LOCATION: (5341)
<223> OTHER INFORMATION: A, T, C or G
<221> NAME/KEY: modified_base
<222> LOCATION: (5400)
<223> OTHER INFORMATION: A, T, C or G

<400> SEQUENCE: 2

```
atctctagag tcgacctgca ggcatgctca aggcctgaca accctgtcgt ttttcgccaa     60
ctcctgcgag gtaacctcga acatgcgctg taagttggcg tagctgtcct gccacgcttn    120
gctgctgttg ttcgtagtgc ctctgtaagc tctctaatgc gctcagaagc tgctgctcca    180
tttcggtcat gaatctcttc accctgatag ataaaaccgc ccagaatcga ttctgtggcg    240
tctgatgagg ttatttggcg ctgtacttga tgacctgacg atgttgagcg ttcttgtact    300
cgtcgatctt cttcgccccc tgcggaagga tcaggtaata cacgctcttg ttcttggaat    360
cgtgaattat cgatacgccg gctccggtct ggctctttaa gtcctgcagg atctggctct    420
gctcgctgat ttcgttctgg cgttcgacca cgatagtccc gagataccaa gctactccaa    480
```

-continued

| | | |
|---|---|---|
| tcaatatcgc aaacaggatc ccacttaatg ccaggctgta cagccatgtc attccgacta | 540 |
| agcggtgtat ctgttttagc tggctgtcgt tctcttcttg gatagcggtc tgtatgttcc | 600 |
| ctgagcttaa tttcaaggcc tcggtgatac gtttctcgtg cttctcgaaa tgcgttcgcg | 660 |
| acgctcgttg cggtagtctt ggcttgctgn cttcgatttg ctctcgaact cccgcgctaa | 720 |
| atttaaaatc tcgctcatac agcactcctt taagcgaat attcgggcca cctgccggat | 780 |
| cagcaatact gatactggat ttggtttccc gtacgaccga caatccggca tcggtaaggt | 840 |
| gggaaatcac ccctttacga tccgtaattt ctccctgctc aatcaagctg attagccctt | 900 |
| tggtaatggc ttccgctgcc tgctgtttgt tgcgaggaag gtcattagag ggggttaatg | 960 |
| ctcggcgatt agcagggtca ttcgggtcgc gtaacccaag ccggtcattg gtgagggttt | 1020 |
| gccatgcgtt aacacgaggc cggtcagccc gatcaaagta aggttgtagc cgttttccgc | 1080 |
| tctgcaattc gatgttcggg ataacaaaat tcaattcaag acgcccttg tcctgatgtt | 1140 |
| gaacccagag gcaggcatac tggtctttat ctagaccggt catcaatgtc tgctcccatt | 1200 |
| catccatcaa tcgctgcttt tcgccttcgg gtaaatcact ctcctgaaaa gagagcacgc | 1260 |
| cagaggtata agttcgggca aattcgcagn catcaatcag ctctttgacg tgctcagggt | 1320 |
| taccccgtaa caccgtcgct tgttcgcgct gacgatcagg gcccagaagg taatcgacag | 1380 |
| gaccactccc gccaccggca ccacgaccat gaatccttaa cgatcacgat gttgctccag | 1440 |
| cagttcggca agatgttggt caatgctatt gagcaccgct aacaacgaca cccgttcttg | 1500 |
| cggcggtaag ccatgctgat tcaagtaacg ggctatttga ttgaggttat taccgatccc | 1560 |
| gctgacctga cgtaacaagg tcgggtctac ggtaaggtta gcggacgacg cccgagctgt | 1620 |
| acgcgattcg cctaagccaa cggctcgtaa ccactcggcc aaatgcttac ggtcacagcg | 1680 |
| ttcaagtagc cgctgatgct ccgcttcggt gagtctgatt ttgatctctt tggtgcgctt | 1740 |
| ttccatgaga atccgctgag aaagtttcgc acccaaagtg cgaattttcg cagtggatgc | 1800 |
| aaggggtttc gggggcggc gagccccctg aaacagtcac agacggcacc tcgaagaggg | 1860 |
| gacgctgtgt gtactgrctt agtacagcat ctatcgtaca tcgaggtcgc atcacgcaca | 1920 |
| aacaaaaagc cccgcaaaag cagggctgtt atctgatata ggttgttttg tctcacacgg | 1980 |
| cagcggaaga ggaatccgaa gtggtactgg tagtagtatt ggatgctgct gacgatattt | 2040 |
| tccgctttga cccaaggctt aaataatcaa tgcctgtaat caacgatctc aatacgcctt | 2100 |
| cggataccat agcgataaac gtatcttgct ggttatggct tgcgatgcaa atcgtagcat | 2160 |
| cacctttttt atactttaaa acacctgcta aatatccatt ttcatctaga acactcttaa | 2220 |
| gatgttcatt tgttattgtt tgtagcgttt gctttgtttc gcttcgagca tacgccttag | 2280 |
| ctagcttccg agaaaaagca tccgcatcat gactatcttt atttactcgc tcaataaatt | 2340 |
| tgcttaagtc aacaaatccc ttaaaacgag tggacatatt gttaacaaaa tcagtggcag | 2400 |
| cattttttat ccatgcttta tagccaaaaa aacgctcgaa acatttggg tcgtagataa | 2460 |
| ataccgtatc gccagcaaaa acaagagatg ccttaccatc aatagaaatc atatcttgat | 2520 |
| ctactcgaga tagttctttt ttgctaaacc cataaaaatt attttcttt cttgataagt | 2580 |
| tttgaactgg atattgcttc ttgtatatgg ttatacaatt gtcgtcatta ttcttactca | 2640 |
| aaacgaaaat gattgagtca acttttgata ttagatccac actgtcaaaa tcaacaattg | 2700 |
| ggatattttc attgccatca ccaccaaacc cagcatcaaa cacaatgcca gtcagaaact | 2760 |
| tcatttgctc attatcatac tgctcagcat catttaaaaa tgaaatggtg ttggtgcggt | 2820 |
| cacttagtgt attaacatct gatactatca caacccgatt ttctaaatca gatatagttt | 2880 |

```
tctttatcac attatcaata atggactgtt ttagctcact gtcatttta aggatggcaa    2940 ttttatagct aaaagagtcc ttagcacccg ctttaccttt attttaaag ttaaagtaag    3000 tgtgcaatgt aacatcgtta atatcacaat caaaatgctt atacagttct aaaagctctt    3060 gtgcttttc ttcattatgc tccaaagcat caagatctta aggcatcgtc actcatcatc    3120
attcctctat gattttttc gcgaacgtta ataatcatc atgatttata actctgataa    3180
aatcattttc ttttattaaa tctttagata aaactatcaa actcaccgtc ttgcgttttt    3240
tcccttccat tagctaccac actgtaagta atcttatagg cagaaacatt aaataatgac    3300
aatgttgggt tgcagtgaat tcttttgtt ttgatgtgca aaaaccgac gataatcaaa    3360 acaaacaaaa aattaactat atttgatggt ttgcttaaat cagtaaagac caacggcatt    3420
atgtacgttg ataaaaaga aagatactca ccggattctt ttttacatga aacgaccttt    3480
aactttcttg acaccgcacc ggagtctaag tttttcaaaa cccatcgata ccaaatgtat    3540
gtataagaac aagttaaaat caaagccccg cagatcactg acctcaatac agaaaatgtt    3600
aatctgctat ttgaatagtc gagtacgcat tgaaattttc catccgcgcc agaacacgaa    3660
gacatggcct tatctaaaac agaccatacg ttatcaatac cagaaaaata tattgttatc    3720
ggtataaaat aaaaacaaca ttgataagag atacattcta attttcattt ttgtaaaatt    3780
tcctgtacca cgttgatcta cttattccta aagaaatcca ttctccatct ctaactttcg    3840
gccttccacc accagagctt ttttttccac gttgacgctg aatttcagaa gtatgtgttt    3900
gtttaacata ctcttcaaag ccaagctctg taaggttctt acttgtccac ttagccacac    3960
ttttagcaat tcccatgact tcgttctcgt ctaaaggtgc ggagaactgc aggttgtagg    4020
ctttagcgcg ttcaatgcag gcttgtagcc attggtcata ctgcggccag ccttggcgga    4080
tagcgcggta agcccacttg cgggttttat cgaagagggt gcagttacgg cctaaaccgt    4140
agtccggcag gatttcgcgg tcattggctg cgccaaggtc gaggtaatcg gctaaccagt    4200
caagggtata gagctctggc tgccagacgg tgatctgcca gtgcaggtgg ttcggattct    4260
tgcaaattag ccctgaatac cccgcatctg cgcccaattt tttacgcagc gcattctcga    4320
tggcggcggc gtatttaagg ggggcagctc gaccatccgg cgcggtacgt accgccgtat    4380
gcaaggcata caacaggtga gcatgtccgt tctcgggtt tttgatggtg agtgtgggcg    4440
caggtgcccc cagatcggcc caatcaatcg cggctccggc tctgtccacg tcaaagcaaa    4500
gccagtacat ggcgtgaggc tgattaaact ggatgtattt tgcgaggaga gcacgctctt    4560
taccggcaat gcgaacacca aactgtaaat catcggagaa gtacggcttg tggggtaacc    4620
ggtcgttaaa aagcgttaaa gcctgattat ccaaggctcc cagccttatg gcggggctgt    4680
tgttttgcac gctgcatgtg ctaatatcct ttctaggttt cgacctagcc ctgaatgtca    4740
tgtccgctcg ccaaagtaga gcatgatttc ggggcttttgt tttttctgcc actaagttac    4800
acctcaacaa cggttttgt catccccgac aatccgttat tcctgcttgt tctcgcacgg    4860
ctttacgctc atactacttc ttgtagatac acttgtcact acatcaagag gtgagatgat    4920
ggccacgatt aatattcgga tcgatgacga gctgaaaagc cgctcttatg ccgcactgga    4980
aaagctgggc gtaacgccgt ccgaggttct gcgccaaaca ctggaatatg tggcccaaag    5040
cggacgtttg ccgttccagc aggttttgct gaccgaggat gatgccgatt tgatggctat    5100
cgttcgggat cgtctggaaa acccacaggc ggggcgtaaa ggtgtcactg gatgagctat    5160
aaccttgaat ttgatccccg agccctgaag aaggaatggc gcaagctcgg ggatgatgtc    5220
```

-continued

| | | | | |
|---|---|---|---|---|
| cgtctgcagt | tcaagaaaaa | actcgagcag | gttctacaac | accccgcgga | tcgataaaaa | 5280 |
| tcgcctgcga | gagctgcatg | actgctacaa | aatcaagctc | cgtgcatccg | gttatcgctt | 5340 |
| nggtctatca | ggttcgcgat | caaaccatta | cggtattcgt | ggtggcggtc | ggtaagggcn | 5400 |
| gagcgttctg | ccgcttacga | tgcggcccga | taaacgctta | taaactcatg | ccgtcaccgc | 5460 |
| gagaataccg | ctgttcgtgc | gcttggctaa | ttgctccaag | cggcgcagtg | ttgtgtttaa | 5520 |
| gctctcgact | tcgtgcgcca | agccggtgac | tt | | | 5552 |